United States Patent [19]
Prokopchak et al.

[11] Patent Number: 5,728,142
[45] Date of Patent: Mar. 17, 1998

[54] METHOD AND APPARATUS OF INCREASING VENOUS BLOOD FLOW TO THE HAND

[75] Inventors: John M. Prokopchak, Lake Hills; Mary K. Crowley; Frank A. Quijano, both of San Antonio, all of Tex.

[73] Assignee: Board of Regents, The University of Texas System, Austin, Tex.

[21] Appl. No.: 622,477

[22] Filed: Mar. 25, 1996

[51] Int. Cl.⁶ .................................................. A61F 7/00
[52] U.S. Cl. .................................... 607/96; 126/204
[58] Field of Search ......................... 126/204; 607/96, 607/108–112, 114; 219/521, 405, 411, 200, 201, 385, 386

[56] References Cited

U.S. PATENT DOCUMENTS

| | | | |
|---|---|---|---|
| 1,110,494 | 9/1914 | Kellogg. | |
| 1,399,095 | 12/1921 | Webb. | |
| 1,703,993 | 3/1929 | Denton | 607/108 |
| 1,740,624 | 12/1929 | Peel. | |
| 3,998,210 | 12/1976 | Nosari | 128/2 H |
| 4,015,591 | 4/1977 | Suzuki et al. | 128/2 R |
| 4,455,479 | 6/1984 | Itoh et al. | 219/411 |
| 4,509,505 | 4/1985 | Mercey et al. | 600/22 |
| 4,796,605 | 1/1989 | Sasaki et al. | 600/22 |
| 4,898,148 | 2/1990 | Urso | 126/204 |
| 4,920,973 | 5/1990 | Tanaka et al. | 128/736 |
| 5,036,179 | 7/1991 | Westerberg et al. | 219/405 |
| 5,045,671 | 9/1991 | Kanaya et al. | 219/405 |

*Primary Examiner*—Robert L. Nasser, Jr.
*Attorney, Agent, or Firm*—Arnold, White & Durkee

[57] ABSTRACT

An apparatus and method for increasing venous blood flow to a human hand is disclosed. The apparatus includes a primary housing having an interior and exterior and a substantially transparent portion, a heating element enclosed in the interior of the primary housing, an opening in the primary housing which permits introduction of a hand into the primary housing, while substantially restricting movement of air between the interior of the primary housing and the exterior of the primary housing, a secondary housing enclosed in the interior of the primary housing, and a control for the heating element. The method includes using the apparatus to heat a patient's hand to permit venepuncture to be performed.

17 Claims, 3 Drawing Sheets

METHOD AND APPARATUS OF INCREASING VENOUS BLOOD FLOW TO THE HAND

BACKGROUND OF THE INVENTION

The present invention generally relates to an apparatus and method for increasing the venous blood flow of a living body. More particularly, the present invention is directed to an apparatus and method for use in increasing the venous blood flow of a human hand, so that venepuncture may occur.

It has been known for some time that increased blood flow to a particular portion of a body will occur upon heating of that particular portion. Low blood flow to a given portion of a body may interfere with medical treatment. For example, if a patient's veins are collapsed, it is very difficult to perform venepuncture to extract blood for testing, or to insert intravenous fluids. Therefore, it would be desirable to develop an apparatus and method to increase the venous blood flow of a patient for improved venepuncture.

A primitive system of increasing blood flow to a human hand is known in the art. Specifically, a closed wooden box in which a heating lamp was placed has been known to be used. A method of using this system included placing a patient's hand in the box and supplying heat by means of the heating lamp. However, several problems developed with the use of this system. First, since the box was closed, it was impossible to view the patient's hand while it was being heated. Therefore, an attendant was required to continually remove and inspect the hand to determine whether the patient was in a condition for venepuncture. Second, there were also many instances of patients being burned by the heating lamp of the apparatus. The primary use of the invention was with diabetic patients, who generally have poor circulation. Thus, diabetic patients could not sense that their hands were being burned by the heating lamp. The prior solution to this problem was to wrap a patient's hand in a towel to prevent burning. However, this did not solve the problem, as the towel-wrapped hand could still contact the heating lamp, causing it to be burned.

SUMMARY OF THE INVENTION

It is therefore an advantage of the present invention to provide an apparatus to increase blood flow in which the patient's extremity is capable of being viewed while inside the apparatus. It is another advantage of the present invention to provide an apparatus in which the heating element is isolated from the patient's extremity, therefore preventing the patient from accidentally contacting the heating element. It is a further advantage of the present invention to provide an apparatus with further safety features to limit the heating element from operating at an undesirably hot temperature.

An exemplary apparatus constructed according to the present invention includes a primary housing having an interior and exterior, a heating element enclosed in the interior of the primary housing, an opening in the primary housing which permits introduction of a hand into the primary housing, and a control for the heating element. Generally, it is desired that the primary housing have at least one substantially transparent portion. The primary housing may be many different shapes and sizes and may be constructed of many different materials. The primary housing may be made of any material capable of withstanding the operating temperature of the apparatus, for example, wood, glass, polycarbonate, insulated steel, lexan, polyurethane, polystyrene, TEFLON, acrylic, plexiglas or the like. The heating element may also be many different shapes and sizes and may be constructed of many different materials. For example, the heating element may be a ceramic heater, a coil heater, heating wire, heating tape, transparent heater, or the like. Further, the heating element may be located at various positions within the primary housing, depending on the heating element used. The control for the heating element may take many different forms. The heating control may be, for example, a microcontroller, a thermostat, rheostat or the like.

The apparatus may further include several safety features, for example, a safety switch, and a secondary housing within the primary housing, so that the heating element is external to the secondary housing. The secondary housing may be many different shapes and sizes and may be constructed of many different materials. The secondary housing may be made of any material capable of withstanding the operating temperature of the apparatus, for example, wood, glass, polycarbonate, insulated steel, lexan, polyurethane, polystyrene, TEFLON, acrylic, plexiglas, or the like. The safety switch may be, for example, a thermal switch, an electromechanical switch such as a relay, thermal snap switch, or the like. Further, the apparatus of the present invention may include a fan assembly disposed in the primary housing to uniformly distribute heat throughout the apparatus.

The present invention also contemplates a method of using the apparatus which includes applying the desired temperature to the apparatus, placing the patient's extremity in the apparatus, viewing the extremity, removing the extremity when it has attained the desired blood flow, and performing venepuncture. The present invention may also be used in conjunction with dialysis treatment. In such a method, the apparatus may be used as a shunt to take over the function of the liver during dialysis treatment.

DETAILED DESCRIPTION

Figure 1:
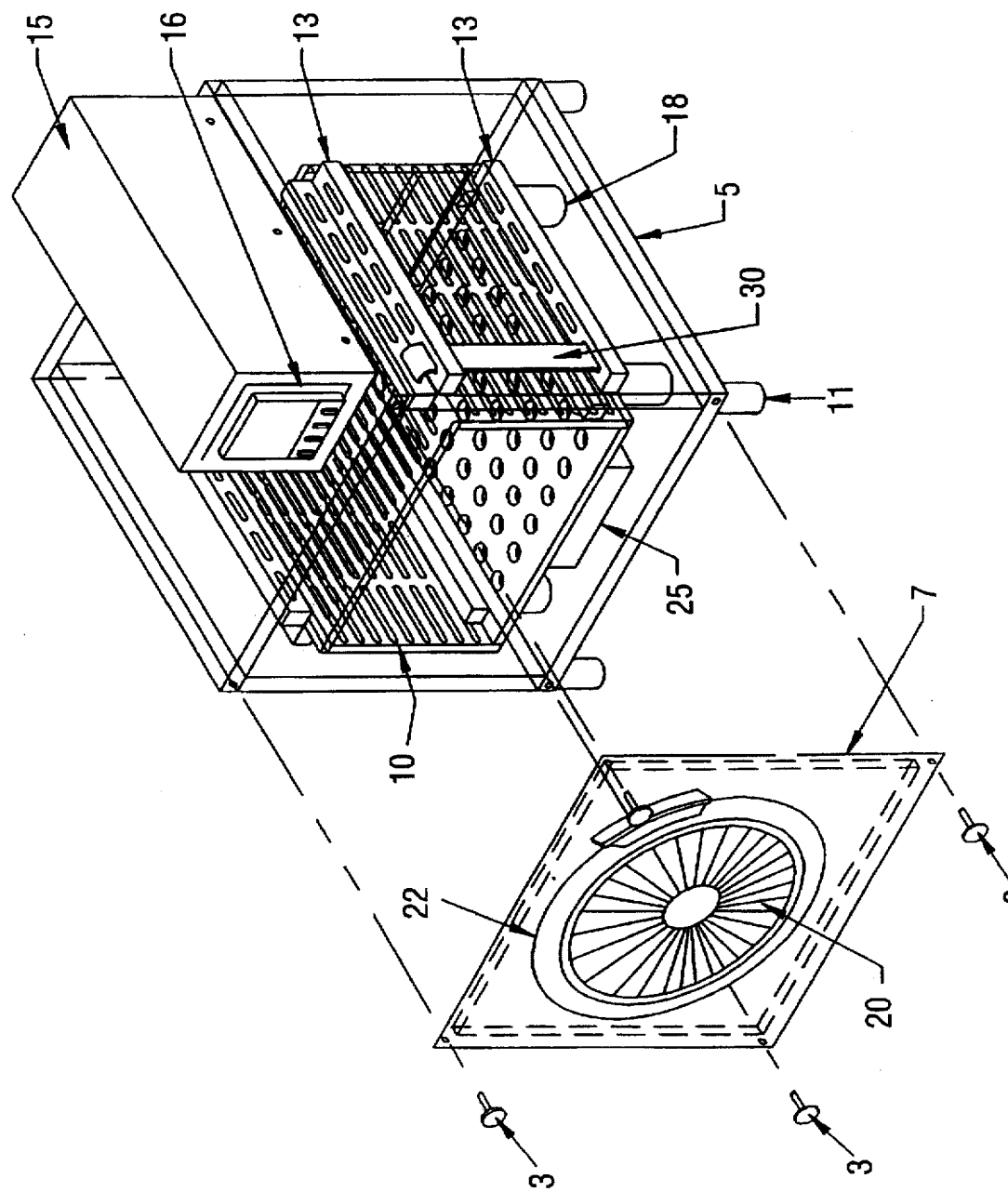
FIG. 1 is a hardware assembly diagram of an apparatus constructed according to the present invention.

FIG. 1 shows an isometric view of an apparatus according to the present invention. The apparatus includes a primary housing 5, a secondary housing 10, heating element control 15, iris opening 20, fan assembly 25, and heating element 30.

The primary housing 5 may be many different shapes and sizes and may be constructed of many different materials. The primary housing 5 may be made of any material capable of withstanding the operating temperature of the apparatus, for example, wood, glass, polycarbonate, insulated steel, lexan, polyurethane, polystyrene, TEFLON, acrylic, plexiglas or the like. In an exemplary embodiment, the primary housing 5 may be rectangular in shape and may be constructed of a clear rigid material, for example, polycarbonate. A material should be selected which is capable of withstanding a temperature somewhat greater than the intended operating range of the apparatus, which is approximately 55°–61° C. In an exemplary embodiment, the primary housing 5 may be constructed of five rectangular portions of polycarbonate, which may be interconnected by means of, for example, fasteners such as screws or bolts, to form a rectangular module having an open end. Alternately, the rectangular portions may be interconnected by a sealing compound, such as glue, rubber cement, or the like.

The apparatus of the present invention may be constructed in different sizes to accommodate patients'extremities, for example, hands or feet. In an exemplary embodiment, the primary housing 5 may be approximately 11 inches high, 10 inches wide, and 12 inches deep. The present invention may be different sizes and be adapted to fit various sizes of hands, feet, or other extremities.

The open end of the primary housing 5 may be closed with a front end portion 7, which may be, for example, another portion of polycarbonate. This front portion 7 may be connected to the rectangular module in any of a number of ways known to those of skill, for example, by knurl knobs 3. Such knobs provide for a quick method of removing the front end for cleaning the interior of the primary housing. Screws, bolts, glue or other fasteners may be used in place of knurl knobs 3. Other methods of connecting the front end 7 to the primary housing 5 may include, for example, a hinged door which is capable of locking closed. The front end 7 further includes an opening through which a patient's extremity may be inserted. A ring 22, capable of rotating, and which may be made of a resilient material, such as TEFLON, polycarbonate, polyvinyl-chloride, polyurethane, polystyrene or the like, is placed within the opening. A gasket may be placed around the ring to properly seal the ring 22 to the front end 7. Further, around this ring, a flexible iris 20, such as is used in a baby incubator, a rubber insert scored with openings, or the like, is attached. In a preferred embodiment, incubator iris model Air Shields, P/N 6812074, may be used. Thus, by rotating the ring 22, the iris enclosure 20 is opened and a patient's extremity may be placed within the apparatus. The ring 22 may then be rotated to close the iris enclosure 20, thereby creating a tight fit around the patient's extremity, substantially sealing the primary housing 5 to maintain the heat level within the housing at the desired temperature.

The primary housing 5 may be raised by means of four spacers 11, which provide for heat to be released from the bottom of the primary housing 5. It is to be noted, however, that the apparatus of the present invention may be used with the front end 7 on a side, on top, or on bottom. In these various configurations, the spacers 11 would be placed to orient the apparatus as desired. The present discussion however is directed to use of the apparatus with the front end 7 parallel to a vertical axis. The heating element control 15 may be attached to the top of the primary housing 5 by means of fasteners such as screws. However, the heating element control 15 need not be on the top of the primary housing and may remain separate from the primary housing.

Located inside of the primary housing 5 is the secondary housing 10. The secondary housing 10 functions primarily as a safeguard by preventing a patient's hand from coming into contact with the heating element 30. The secondary housing 10 may be many different shapes and sizes. In a preferred embodiment, the secondary housing 10 may be a rectangular structure which is open at the front. Alternately, the secondary housing 10 may be open at the front and rear. The secondary housing 10 may be made of any material capable of withstanding the operating temperature of the apparatus, for example, wood, glass, polycarbonate, insulated steel, lexan, polyurethane, polystyrene, TEFLON, acrylic, plexiglas or the like. In an exemplary embodiment, the top, side and rear panels may be constructed of, for example, polycarbonate, and the bottom panel may be constructed of, for example, TEFLON. However, it is possible to construct all of the panels of any one or more of the above described materials, or any other material capable of withstanding the temperature range of the apparatus. Generally, it is desired that the secondary housing 10 have at least one substantially transparent portion. The panels may be connected by means of fasteners such as screws, as discussed above, or joined by a sealing compound, such as glue or rubber cement. To aid in heat conduction and uniformity of temperature, one, several or all of the panels may be slotted with openings. The slotted openings may be many different sizes and shapes. For example, the bottom panel may include a pattern of circular holes. The top and side panels may be slotted with, for example, a rectangular pattern. Further, the secondary housing may be raised from the bottom of the primary housing by means of spacers 18, which may be made of TEFLON, for example.

The heating element 30 may be many different shapes and sizes and may be constructed of many different materials. For example, the heating element may be a ceramic heater, a coil heater, heating wire, heating tape, transparent heater or the like. Depending on the type of heater selected, the heating element 30 may be placed below, above, on the side of, or around the perimeter of the secondary housing 10. For example, a ceramic heater or a coil heater may be placed below the secondary housing 10. Alternately, a heating wire or heating tape may be placed around the perimeter of the secondary housing 10.

In an exemplary embodiment, the heating element 30 may be wrapped around the exterior of secondary housing 10. Although shown only partially in FIG. 1, it is to be understood that heating element 30 may be continuous and extend around the exterior of the top, sides, and bottom panels of secondary housing 10. The heating element 30 may be, for example, a flexible heating tape, such as Omega P/N SRT051-120. Preferably, the heating element will be a continuous segment, approximately 12 feet long and ½ inch wide. However, the present invention may utilize heaters that are connected in parallel or in series. In the exemplary embodiment shown, the heating tape 30 is fed through spacer members 13 which are affixed around the perimeter of the secondary housing 10. These spacer members 13 may be slotted with openings to receive the heating element 30. However, spacer members 13 are not necessary, and the heating element 30 may be directly attached to the exterior of the secondary housing 10. Although not required by the present invention, a means may be provided to uniformly distribute heat within the primary housing 5. For example, a fan assembly 25 may be placed external to the secondary housing 10. The fan 25 may be various commercially available fans, such as a Papst model number 8506N. Preferably, the fan 25 is placed underneath secondary housing 10, thereby aiding in delivering a uniform temperature flow to a patient's hand. Instead of a fan assembly, several slotted openings on the sides, back or bottom of the primary housing may be used to uniformly distribute heat throughout the primary housing 5.

Figure 2:
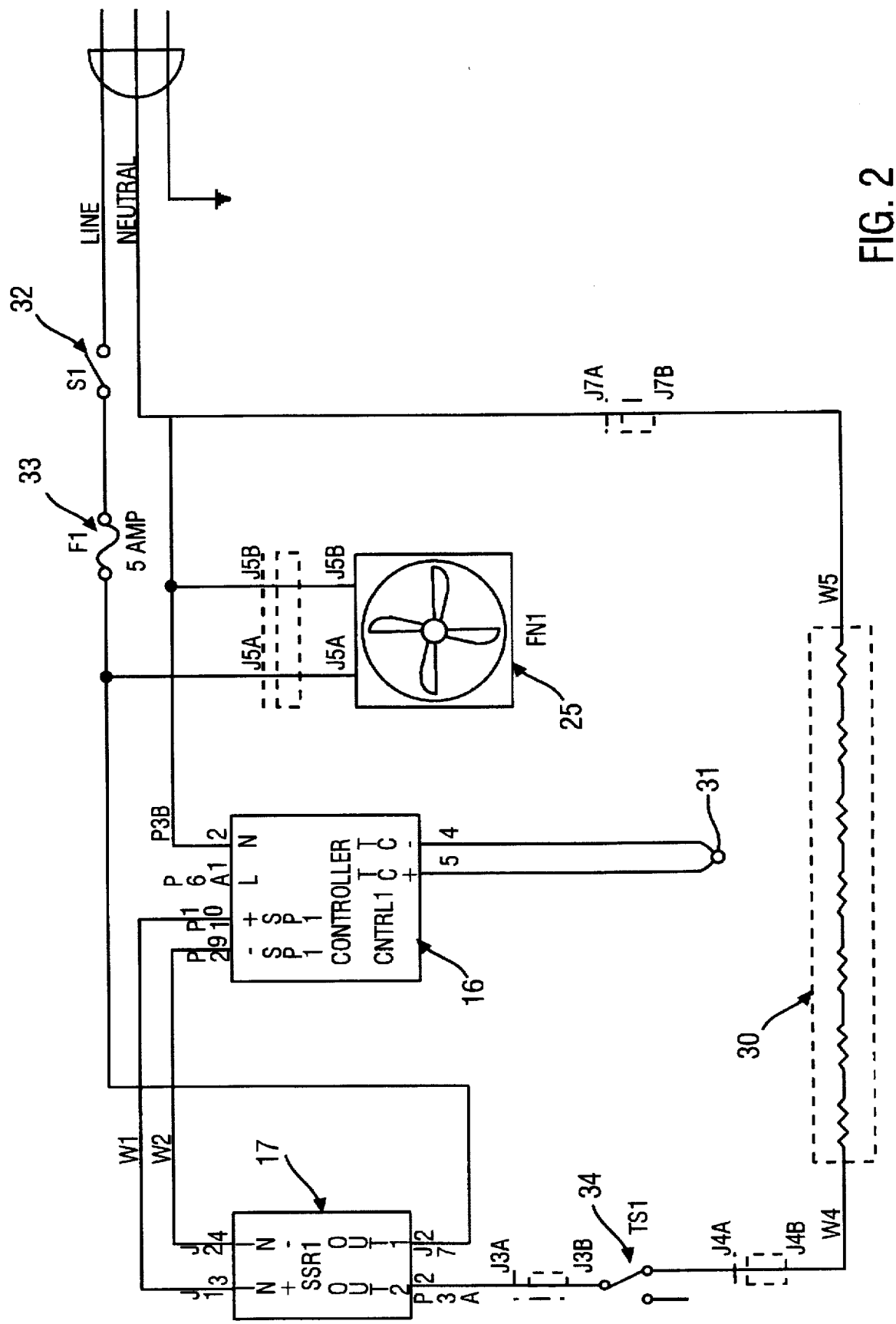
FIG. 2 is an electrical schematic diagram of an apparatus according to the present invention.

The heating control 15 may be, for example, a microcontroller, a thermostat, rheostat or the like. In an exemplary embodiment, heating element control 15 will be a microcontroller that may include for example, a temperature controller 16 and a solid state relay 17. The controller 16 may be, for example, a miniature microprocessor temperature controller, such as Omega, CN9121A. The controller 16 is preferably selected to operate within a 0.1° C. resolution up to a temperature of 200° C. A user can control the temperature of the apparatus by means of the main display of the heating element control 15, which may include, for example, a plurality of user function keys. A temperature sensor 31, as shown in FIG. 2, supplies controller 16 with actual temperature data of the apparatus. This sensor may be, for example a thermocouple, thermopile, thermistor, ceramic or glass RTD element, thin film detector or the like. The thermocouple 31 is preferably placed within the apparatus, and more preferably, at the rear and vertical middle of the primary housing 5. This location permits the thermocouple 31 to detect the temperature at a close proximity to a patient's hand. Controller 16 will then send signals based on the actual unit temperature and the desired unit temperature to solid state relay 17, which will output power to heating element 30 based on this temperature. The solid state relay 17 may be, for example, a direct current solid state relay (SSR), such as the OMEGA SSR240D10.

FIG. 2 is an electrical schematic diagram of one potential manner of producing an apparatus of the present invention. Power is supplied through a normal outlet connection. When the power switch 32 is turned on, power is supplied through fuse 33 to fan 25 at J5, temperature controller 16 at P6, and solid state relay 17 at J7. Controller 16 also receives temperature information from thermocouple 31. Controller 16 develops control signals based on the desired temperature programmed by the user and the actual temperature received from the thermocouple 31. These control signals are output on P1 and P2 and are input to solid state relay 17 at J1 and J2. The solid state relay 17 then outputs power to the heating element 30 over P3. As a further safety precaution, a safety switch 34, which may be a thermal switch such as a thermal cutoff, is placed in between the solid state relay 17 and heating element 30. The thermal switch 34 may be located at any location within the primary housing 5. In a preferred embodiment, however, the thermal switch 34 may be located underneath the secondary housing 10. Thermal switch 34 may be, for example, a thermo switch such as Cole-Parmer P/N AD147-12/150° F., and it may be set to open the line, thereby turning off power to the heating element 30, when the actual temperature in the apparatus reaches 66° C., to prevent overrun of the heating element 30 and to prevent injury the patient.

In the illustrative embodiment, operation of the apparatus is controlled through a main control panel on the front face of heating element control 15. To begin operation, the MAIN POWER switch is turned on. Temperature is set by holding the STAR button on the main control panel and increasing or decreasing the temperature by using the up or down ARROW buttons. After the desired temperature is set, the unit is preferably allowed to run for approximately 30 minutes to stabilize at the desired temperature. The desired temperature is in the range of 55-61° C., and more preferably at 58° C. However, individual patients may require slightly more or less heat to achieve the benefits of this invention.

The controller may be programmed to be permanently set at a given temperature, such as 58° C. according to the following steps:

1. Behind the lower front bezel of the controller 16 is a JUMPER. The JUMPER is located on the left-most pins (Locked position). Reposition the JUMPER to the right-most pins (Unlocked position).
2. Press P button to convert the main display of the controller 16 from temperature read-out to the function/option mode. The function digit will begin to flash. To change from function 0.0 to 0.3 press the UP button to increment to the desired function.
3. Press STAR button to change flashing function digit to option mode. The option digit will flash. To change from option 0.3 to 1.3 press the UP button.
4. Press STAR button to function made, and increment the UP button to function 24.
5. Press the STAR button to change flashing function digit to option mode. Change the option digit to the temperature needed to be locked in (in this case, 61° C.). Press the UP button and increment to 61.24.
6. Press P button when finished selecting the functions and options. Display will go back to normal.

In addition, the parameters may be mechanically locked into memory by removing the JUMPER behind the lower front bezel of the controller 16.

As a further safety precaution, it is recommended that a user place a reference thermometer, preferably a NIST certified thermometer, in the center of the unit during stabilization. The temperature of the reference thermometer will increase higher than the temperature shown on the heating element control 15 main control panel, and possibly read as much as 10-12° C. degrees higher before stabilizing to the set operating temperature.

After the apparatus has reached the desired temperature after the stabilization period, the patient procedure may begin. Ring 22 around the iris enclosure 20 is rotated to open iris enclosure 20. Next, a patient's extremity is introduced into the secondary housing 10. Preferably this extremity will be a hand, but the present apparatus may also be used with a patient's foot or forearm or leg. After introduction of the hand, ring 22 is rotated to close, thereby maintaining a relatively tight seal around the patient's hand. The patient's hand can be viewed from above or aside the apparatus. When it appears that the desired blood flow has been achieved, and the patient's veins are nearer the surface, the hand may be removed from the apparatus. Typically, this occurs on the order of approximately 10-15 seconds after introduction of the hand to the apparatus. After the hand is removed, venepuncture may be performed on the patient.

Figure 3:
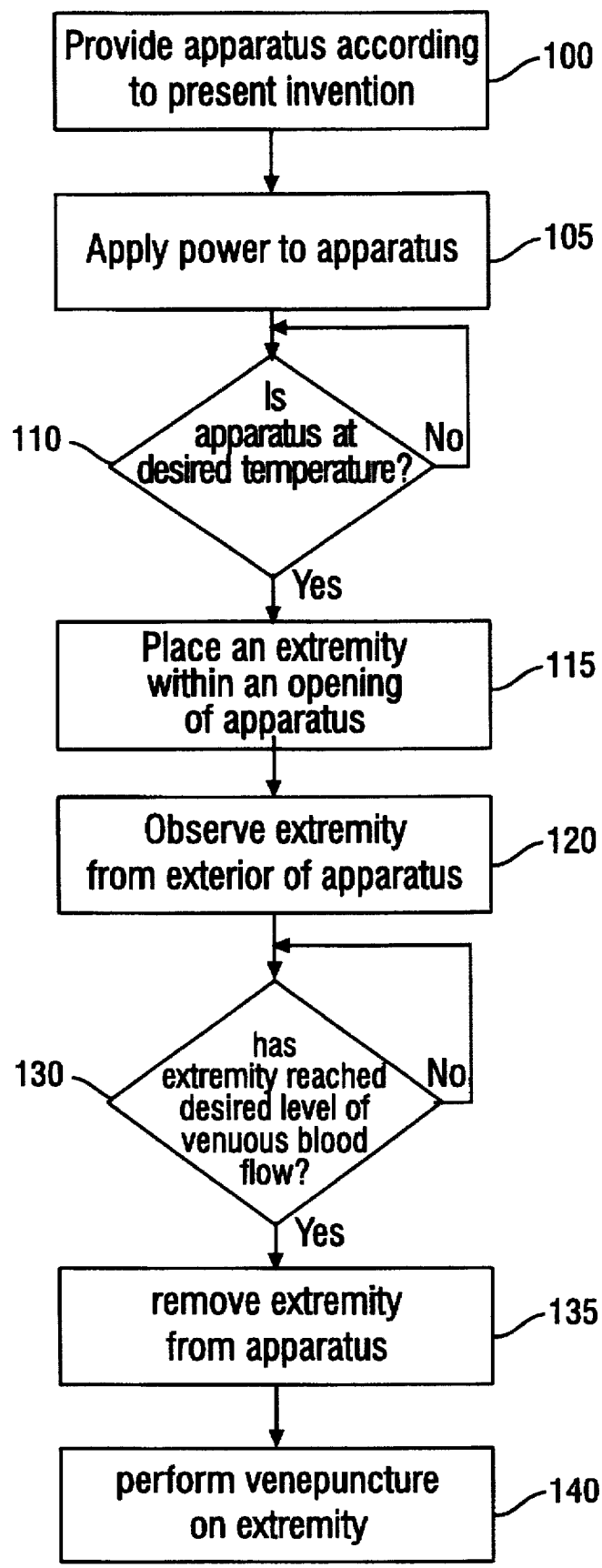
FIG. 3 is a flow chart diagram of a method according to the present invention.

FIG. 3 shows a flow chart of a method according to the present invention. In step 100, an apparatus according to the present invention is provided. In step 105, power is applied to the apparatus, thereby placing the apparatus in an operating condition. The apparatus is set for a desired temperature, which in an exemplary embodiment may be between 55°-61° C. In step 110, the temperature of the apparatus is examined to determine whether the desired temperature has been attained. If the desired temperature has not been attained, step 110 is repeated until the desired temperature has been attained. Once the desired temperature has been attained, step 115 comprises placing a patient's extremity within an opening of the apparatus. In step 120, the extremity is observed from the exterior of the apparatus. In step 130, an operator may determine whether the extremity has reached the desired level of venous blood flow. If it has not, step 130 is repeated until the desired level is reached. If the patient's extremity has reached the desired level of venous blood flow, the extremity is removed from the apparatus in step 135. A further step of 140 may include performing venepuncture on the extremity.

In an alternate method of use after venepuncture, a patient's hand may be placed back in the apparatus. This method may be performed when the system is used in conjunction with treating liver and pancreatic disorders.

Further modification and alternative embodiments of this invention will be apparent to those skilled in the art in view of this description. Accordingly, this description is to be construed as illustrative only and is for the purpose of teaching those skilled in the art the manner of carrying out the invention. It is to be understood that the forms of the invention herein shown and described are to be taken as the presently preferred embodiments. Various changes may be made in the shape, size, and arrangement of pans. For example, equivalent elements or materials may be substituted for those illustrated and described herein, and certain features of the invention may be utilized independently of the use of other features, all as would be apparent to one skilled in the art after having the benefit of this description of the invention.

What is claimed is:

1. An apparatus for increasing venous blood flow of an extremity of a patient comprising:

a primary housing having an interior adapted to receive said extremity in which said increased venous blood flow is desired, an exterior, and a substantially transparent portion;

a heating element positioned in the interior of the primary housing;

a secondary housing disposed within said primary housing and adapted to receive said extremity, wherein at least a portion of said extremity is visible within said secondary housing when said portion is positioned in said secondary housing, said secondary housing being configured to prevent said extremity from contacting said heating element;

an opening in the primary housing which permits introduction of said extremity into the primary housing; and a programmable control for the heating element for setting an interior temperature of the primary housing at a level that is not harmful to the patient.

2. The apparatus of claim 1, further comprising a safety switch contained within the primary housing.

3. The apparatus of claim 2, in which the safety switch is a thermal safety switch, said thermal safety switch adapted to prevent injury to said extremity by turning off power to said heating element if said interior temperature exceeds approximately 66 degrees Celsius.

4. The apparatus of claim 1 wherein the heating element is located between a portion of the secondary housing and a portion of the primary housing.

5. The apparatus of claim 1 further comprising a fan assembly disposed in the primary housing.

6. An apparatus as claimed in claim 1 in which the control for the heating element includes a temperature controller.

7. An apparatus as claimed in claim 1 in which the control for the heating element includes a solid state relay.

8. An apparatus as claimed in claim 1 in which the control for the heating element includes a thermocouple.

9. An apparatus as claimed in claim 1, in which the heating element is selected from the group of heating coil, ceramic heater, heating wire, transparent heater, and heating tape.

10. An apparatus as claimed in claim 1 in which the heating element comprises heating tape said heating tape being laced about an exterior of said secondary housing.

11. An apparatus as claimed in claim 1, in which the opening is adapted to substantially restrict movement of air between the interior of the primary housing and the exterior of the primary housing.

12. An apparatus as claimed in claim 11 in which the opening comprises an iris enclosure, said iris enclosure configured to form a tight fit around said extremity, thereby minimizing heat loss from said apparatus.

13. An apparatus for increasing venous blood flow to a human extremity, comprising:

a primary housing having an interior, an exterior, and a substantially transparent portion;

a secondary housing having a substantially transparent portion and being disposed within the primary housing, said secondary housing being adapted to receive said extremity;

a heating element enclosed in the interior of the primary housing and external to the secondary housing;

wherein said secondary housing is configured to prevent said extremity from contacting said heating element;

a variable opening in the primary housing which permits introduction of said extremity into the primary housing, said variable opening configured to form a tight fit around said extremity, thereby minimizing heat loss from said apparatus a programmable control for the heating element; and a safety switch adapted to prevent injury to said extremity by turning off said heating element if said interior exceeds a predetermined temperature.

14. The apparatus of claim 13, further comprising a fan assembly disposed in the primary housing.

15. An apparatus as claimed in claim 13 in which the programmable control for the heating element comprises a temperature controller.

16. The apparatus of claim 13, further comprising spacers attached to said secondary housing, said spacers configured to displace said housing with respect to said primary housing.

17. The apparatus of claim 13, wherein said predetermined temperature is approximately 66 degrees Celius.

* * * * *

UNITED STATES PATENT AND TRADEMARK OFFICE
CERTIFICATE OF CORRECTION

PATENT NO.    :   5,728,142
DATED         :   March 17, 1998
INVENTOR(S)   :   Prokopchak et al.

It is certified that error appears in the above-identified patent and that said Letters Patent is hereby corrected as shown below:

In claim 10, column 8, line 6, after 'tape' insert --,--.
In claim 17, column 8, line 49, delete "Celius" and insert --Celsius-- therefor.

Signed and Sealed this

Sixteenth Day of June, 1998

Attest:

BRUCE LEHMAN

*Attesting Officer*　　　*Commissioner of Patents and Trademarks*